US00RE35484E

United States Patent [19]

McLaughlin

[11] E Patent Number: Re. 35,484

[45] Reissued Date of Patent: Mar. 25, 1997

[54] LIGHT ACTIVATED COLORATION OF DENTAL RESTORATIONS

[76] Inventor: Gerald G. McLaughlin, 12 Cottonwood Ave., Port Jefferson Station, N.Y. 11776

[21] Appl. No.: 337,554

[22] Filed: Nov. 10, 1994

Related U.S. Patent Documents

Reissue of:

[64] Patent No.: 5,162,130
Issued: Nov. 10, 1992
Appl. No.: 851,029
Filed: Mar. 9, 1992

U.S. Applications:

[63] Continuation-in-part of Ser. No. 441,371, Nov. 27, 1989, Pat. No. 5,094,619, which is a continuation-in-part of Ser. No. 225,713, Jul. 28, 1988, abandoned, which is a continuation of Ser. No. 943,927, Dec. 17, 1986, abandoned.

[51] Int. Cl.[6] ..... A61C 5/10; A61C 13/08; B29C 39/12

[52] U.S. Cl. ..... 427/2.26; 264/20; 264/78; 264/129; 264/246; 264/482; 264/494; 427/2.27; 427/2.29; 427/553; 427/555; 427/557; 427/558; 433/203.1; 433/215; 433/217.1; 433/223

[58] Field of Search ..... 264/16, 19, 20, 264/405, 432, 494, 78, 129, 132, 245, 246; 427/2.26, 2.27, 2.29, 553, 555, 557, 558, 160; 433/203.1, 215, 217.1, 223

[56] References Cited

U.S. PATENT DOCUMENTS

| | | | |
|---|---|---|---|
| 4,585,417 | 4/1986 | Sozio et al. | 264/328.18 X |
| 5,024,790 | 6/1991 | Grossman et al. | 264/20 X |
| 5,030,392 | 7/1991 | Grossman et al. | 264/20 X |
| 5,040,964 | 8/1991 | Oppawsky et al. | 264/16 X |
| 5,094,619 | 3/1992 | McLaughlin | 264/20 X |
| 5,104,591 | 4/1992 | Masuhara et al. | 264/16 |
| 5,110,513 | 5/1992 | Puvilland | 264/19 |

*Primary Examiner*—Karen Aftergut
*Attorney, Agent, or Firm*—Galgano & Burke

[57] ABSTRACT

A method of effecting the coloration of a restoration to be mounted on a tooth including the steps of forming a mixture of powdered dental porcelain and a photonucleable silicate glass and shaping the mixture into a dental restoration. The dental restoration is heated in an oven to its fusing temperature and allowed to cool. Selected areas of the restoration are exposed to ultra-violet light. The dental restoration is reexposed to high energy while the color of the selected areas changes.

20 Claims, No Drawings

LIGHT ACTIVATED COLORATION OF DENTAL RESTORATIONS

Matter enclosed in heavy brackets [ ] appears in the original patent but forms no part of this reissue specification; matter printed in italics indicates the additions made by reissue.

BACKGROUND OF THE INVENTION

This application is continuation-in-part of my application Ser. No. 07/441,371 filed on Nov. 27, 1989, now U.S. Pat. No. 5,094,619, which is a continuation-in-part of 07/225,713 filed on Jul. 28, 1988, now abandoned, which is a continuation of 06/943,927 filed on Dec. 17, 1986, now abandoned.

This invention relates to the coloration of dental restorations and more particularly to methods of altering the coloring of dental restorations to obtain a matching or otherwise desired color. By dental restoration herein is meant any configuration of material designed to improve the appearance or function of a tooth or teeth. This would include fillings, bridges, crowns, dentures, etc.

Present techniques for obtaining the desired color of restorations involve either having the coloring agent incorporated into the material itself at the time of formulation, or applying the coloring agent as a coating after the restoration has been manufactured. Typical of proposed methods of incorporating the coloring agent within the restoration material prior to preparing the restoration is shown in U.S. Pat. Nos. 4,433,959 and 4,563,153. U.S. Pat. No. 4,481,227 shows a method of adding the coloration agent to restoration after the latter is prepared.

All of these methods have severe drawbacks. When the coloring agent is incorporated into the material, typically in the laboratory where the restoration is manufactured, the color is essentially established before it can be viewed in its final form so it is difficult if not impossible to match the color and shading of the restoration perfectly with the tooth on which the restoration is to be mounted. Coating techniques also generally require preparation in the laboratory with the similar difficulty to obtain an acceptable, if not a perfect, match.

In my earlier patent application identified above, there is described and claimed a method for altering the color of a polymerized dental restoration through the application of heat.

SUMMARY OF THE INVENTION

The present invention relates to the use of energy in the light portion of the electromagnetic wave spectrum to alter the color or hue of a porcelain dental restoration.

According to the principles of this invention, a material having the capability of having its color altered with the application of light is incorporated into the porcelain mixture making up the restoration prior to its fabrication. The color of the restoration material after being cured (that is, hue, chroma, or value) is then altered with the application of light to obtain the desired color.

In accordance with the principles of this invention, one preferred embodiment consists of a method of coloring a dental restoration which comprises the steps of incorporating into a standard dental porcelain a photosensitive or photonucleable material to form a ceramic restoration which is fired to its fusing point and then cooled. The restoration is formed using conventional techniques except that the completed restoration contains the photosensitive or photonucleable material.

The areas of the restoration selected to undergo a color change are exposed to ultra-violet light which apparently forms color centers in the photonucleable material. The restoration is then heated either in a furnace or the selected areas are exposed to some other source of energy such as light of a different frequency to cause growth in the color centers and intensification of the color in the restoration. The source of heat or other energy is withdrawn when the appropriate shade or color has been reached and the restoration is allowed to cool.

One of the features of this invention is that growth of the color centers or intensification of the color in the restoration can be brought about by the application of a laser beam to deliver heat to the selected areas of the restoration while the restoration is in the mouth of the patient.

It is thus a principal object of this invention to provide a method of coloring a porcelain dental restoration capable of producing a better color match with the tooth on which the restoration is to be permanently mounted.

Other objects and advantages of this invention will become more obvious from the following description of the preferred embodiments of this invention.

DETAILED DESCRIPTION OF THE PREFERRED EMBODIMENTS

In the manufacture of fillings, crowns and other dental restorations, composition materials or porcelain are often employed. A typical or standard dental porcelain powder from which such restorations may be made is sold under the trade mark of "Air Fired Porcelain" by Excelco Corp. of Deerfield Beach, Fla., and is described in U.S. Pat. No. 3,052,982. A similar material is sold by Johnson and Johnson under the name of "Ceramco II".

In accordance with the principles of this invention, a standard dental porcelain powder such as that identified above is mixed in roughly equal proportions by weight with a photonucleable, crystallizable, lithium silicate glass whose basic composition is described in U.S. Pat. No. 5,062,877. Such material is well known in the industry and is marketed by Corning Corp., Corning, NY, as Corning Code 8603 under the names "Fotoform" and "Fotoceram". Fotoform is described in U.S. Pat. No. 2,628,160 and Fotoceram is described in U.S. Pat. No. 2,971,853 and both come within a class of glass described as photonucleable, crystallizable, lithium silicate glass.

The porcelain and photonucleable material are mixed approximately in equal proportions by weight, and then the powdered mixture is formed into a ceramic restoration using conventional techniques for the porcelain alone, heated in an oven to its fusing point and then allowed to cool.

After cooling, selected areas of the restoration exposed to light having an ultra-violet component in the range of 280–340 nm. wavelength. This exposure apparently establishes color centers or nuclei in the restoration. The restoration is then reheated and held for a particular period of time during which time the areas exposed to the light will gradually change color, apparently due to growth in the color centers resulting in color intensification. When the appropriate shade or color is reached, the restoration is allowed to cool under ambient conditions.

The following are examples of my invention:

EXAMPLE 1 a. A sheet of Fotoform is ground into a fine powder.

b. This powder is mixed in equal proportions by weight with the dental porcelain powder Air Fired Porcelain described above. It has been found that the actual proportions of the mix are not critical. However, more subtle but natural final colors are achieved by increasing the proportion of standard dental porcelain powder, so long as the amount of the silicate powder is not so small that the particles are blocked from the light when exposed as will be described below.

c. Using the standard dental laboratory technique for dental porcelain powder [ajone] *alone*, a ceramic restoration is formed from the mix. This can be on a metal matrix such as dental gold alloy, or non-precious dental alloy, or even platinum foil as is understood in the art. Additionally, this mixture can be used on an investment model. In other words, this powder is used the way standard dental porcelain powders are used.

d. Once formed, the restoration is fired in an electric furnace to its fusing point which is approximately 871 deg C, and then allowed to bench cool. The rate or heat rise should be 45 to 60 deg. C. per minute depending upon the exact formulation of the porcelain mixture which is slow enough to allow penetration of the heat but fast enough to minimize the total heat time. This step does not differ from what the laboratory technician would perform were he using the standard dental porcelain alone.

e. After cooling, the appearance of the finished restoration is the same as if the silicate material had not been used, except for a slight increased translucency. The areas of the restoration which will be visible after the restoration is installed in the patient and which needs to be altered are exposed to a 3500 watt mercury arc lamp with a parabolic reflector from a distance of 21 inches for an exposure of approximately one second. This produces an extremely bright light with a high ultra-violet (UV) component including the range around 280–340 nm wavelength. The areas which are not to be exposed to this light are masked by painting the surface with a opaque suitable material such as "separating liquid" which is available from Whip Mix Co. of Louisville, Ky. Any other suitable opaque material may be employed. The surface can also be masked with opaque tape or any other means which are available.

f. The restoration is then placed back into the furnace. The temperature is raised relatively quickly to approximately 500 deg. C, and then raised to the fusing temperature at the rate of approximately 5 deg. C. per minute and no more than about 10 deg. C. per minute. At around 600 deg. C. the exposed areas take on a pink hue while the other areas remain unchanged. At around 700 deg. C. the pink hue disappears, and the areas become less intense in color (ie, whiter). As 800 deg. C. is approached, the exposed areas become grey and then black. The fusing temperature which is above 800 deg. C. when reached is then held for about 30 minutes during which time the color which develops in the areas intensifies. The exposed areas will take on the shade of an off white, or "dental brown". The restoration is removed from the oven when the right shade (that is, hue and intensity) is present and bench cooled, and the restoration will retain that color. It has been found that by reducing the proportions of the silicate material in the initial mixture the effects or the temperature changes are less pronounced and more subtle.

EXAMPLE 2 a. and b. The steps as described in the previous example are repeated.

c. The resulting powder mixture is formed into a block by placing it into a mold made of investment material and then placed into a vacuum furnace. The temperature is raised to the fusing point of the mixture. The rate of temperature rise is approximately 55 deg. C. per minute. Once the powder fuses into a solid block, the block is allowed to bench cool.

d. The block of porcelain mixture is removed from the mold by breaking the mold and sandblasting any residue from the surface of the block.

e. The block is then glued to an appropriately shaped metal stem so that it can be used in a milling machine.

f. The block is milled to the shape of the desired dental restoration.

g. Once formed through the milling process, the change in color of selected areas is accomplished by following steps e–f in Example 1.

EXAMPLES 3 and 4

These examples are the same as Example 1 except that in place of Fotoform, the material Fotoceram is used. The result of this change is that the appearance after forming the restoration and before exposing to ultra-violet light is whiter and denser than that which would be expected using the pure dental ceramic alone.

EXAMPLE 5 a. A mixture of finely ground Fotoform glass and clear dental glaze in equal parts by weight is prepared. (A dental porcelain stain may be added to the mixture or substituted for the glaze. The proportion is not critical when clear glaze is used.) Note: When dense stains are being used, the proportion of Fotoform must be increased. A reasonable proportion with the dense white stain titanium oxide is 4 parts Fotoform to 1 part stain, by weight.

b. This mixture is applied to the surface of a porcelain dental restoration by using a small wet brush. The standard technique for applying simple stains is employed. The restoration must be made from a dental porcelain with a fusing temperature above 700 deg. C. The mixture has a fusing temperature lower than that of the restoration.

c. The restoration is warmed sufficiently to dry the stain in few minutes. Typically this would be accomplished by placing the restoration at the door of the furnace.

d. Once thoroughly dry, the restoration is placed into the oven and air fired, the temperature being raised at a rate of about 55 deg. C. per minute until about 648 deg. C, the fusing temperature of the mixture, is reached. The oven is turned off and when the temperature drops back to 160 deg. C. the restoration is removed to allow it to bench cool. At this point the restoration looks as if it were stained and/or glued in the usual manner.

e. Selected areas of the restoration are exposed to a 3500 watt mercury arc lamp with a parabolic reflector from a distance of 21 inches for an exposure of approximately one second. This produces an extremely bright light with a high ultra-violet component including the range of around 280–340 nm wavelength. The areas not to be exposed are masked in the manner previously described. No change in color occurs during this exposure.

f. The restoration is then placed back into the porcelain furnace for reheating. The temperature is quickly raised to approximately 500 deg. C, and then raised to 615 deg. C. at the rate of no more than about 5 deg. C. per minute. The temperature is held there for approximately 30 minutes. During this time, the areas of the restoration which were exposed to the light gradually take on a pink hue while the other areas remain unchanged. This pink hue will interact with original color of the glaze or stain put on the restoration described in step b to produce a greater intensity of the original hue if the original dominant hue was pink. If the original dominant hue was not pink, the new shade will exhibit less green and will have lowered value, ie, that is be more grey. By increasing the proportion of the Fotoform to the stain/glaze material, the changes brought upon by the pink hue become more pronounced.

EXAMPLE 6

In place of Excelco "Air Fired Porcelain", the dental Porcelain Ceramco II produced by Johnson and Johnson was used. All steps were the same as in Example 1 except that initial firing of the restoration is performed in a vacuum furnace. This results in a denser and slightly more visually pleasing translucent result. All temperatures are the same, except that the first firing goes to 954 deg. C.

EXAMPLE 7

The steps of example 1 are repeated, but with the substitutions described in Example 6.

EXAMPLES 8 and 9

These are the same as Examples 6 and 7, respectively, except that Fotoceram is used in place of Fotoform.

EXAMPLES 10–18

These are the same as examples 1–9, respectively, except that a high powered ultra-violet laser is employed in place of the 3500 watt mercury arc lamp. This laser can be hand-guided or computer-guided.

EXAMPLES 19–27

These are the same as Examples 10–18 except that the reheating step is conducted using a high powered laser of significantly lower frequency below the ultra-violet spectrum to heat up the areas previously exposed to the first laser.

While only certain preferred embodiments of this invention have been described, it is understood that many variations of this invention are possible without departing from the principles of this invention as defined in the claims which follow.

What is claimed is:

1. A method of effecting coloration of a dental restoration to produce a desired color in selected areas of said dental restoration comprising the steps of:

(a) forming a mixture of powdered dental porcelain and a photonucleable silicate material;

(b) shaping said mixture into said dental restoration;

(c) heating said dental restoration to its fusing temperature and thereafter allowing said restoration to cool;

(d) exposing selected areas of said restoration to light of a specific wave length to establish color centers in said restoration;

(e) reheating said selected areas to a predetermined temperature sufficient to cause color intensification in said selected areas of said restoration and maintaining said predetermined temperature while said color intensifies and changes in said selected areas to produce said desired color in said selected areas; and (f) cooling said restoration after said desired color of said selected areas is produced to thus prevent further color intensification of said color centers in said dental restoration.

2. The method of claim 1 wherein said powdered dental porcelain and said photonucleable silicate material are mixed in approximately equal proportions by weight.

3. The method of claim 1 wherein said dental restoration is heated at a rate sufficiently slow to allow penetration of heat into said dental restoration and said dental restoration is bench cooled after heating.

4. The method of claim 3 wherein said selected areas of said restoration are exposed to UV in a range of about 280–340 nm wavelength to established said color centers.

5. The method of claim 4 wherein said dental restoration after exposure to UV is reheated at a rate of no more than about 10 deg. C. per minute to said fusing temperature and is held at said fusing temperature for a predetermined period of time to allow said color to intensify.

6. The method of claim 5 wherein said reheated dental restoration is bench cooled.

7. The method of claim 1 wherein said light is a laser.

8. The method of claim 4 wherein said reheating is effected by exposing said selected areas to laser light at a frequency below that of a UV spectrum.

9. The method of effecting coloration of a dental restoration to produce a desired color in selected areas of said dental restoration comprising the steps of:

(a) forming a mixture of dental glaze or dental stain and a photonucleable silicate material;

(b) applying said mixture to a surface of a porcelain dental restoration having a fusing temperature above a fusing temperature of said mixture;

(c) heating said coated dental restoration to a temperature below said fusing temperature of said restoration and above said fusing temperature of said mixture and thereafter allowing said restoration to cool;

(d) exposing selected areas of said restoration to a source of electromagnetic energy to establish color centers in said mixture applied to said dental restoration:

(e) applying additional energy to said dental restoration to cause growth in said color centers resulting in intensification of color of said selected areas of said coated dental restoration to produce said desired color in said selected areas; and (f) withdrawing said growth causing energy from said restoration after said desired color of said selected areas is produced to thus prevent further color intensification of said color centers in said mixture applied to said dental restoration.

10. The method of claim 9 wherein said energy causing said establishment of said color centers in said mixture comprises light in a specific frequency.

11. The method of claim 10 wherein said light is in UV spectrum.

12. The method of claim 11 wherein said ultra-violet light is in a range or about 280–340 nm wavelength.

13. The method of claim 12 wherein said ultra-violet light has an intensity on said restoration of about that obtained from a 3500 watt mercury arc lamp with a parabolic reflector at a distance of about 21 inches from a site of application to said dental restoration.

14. The method of claim 13 wherein said additional energy application is effected by exposing said selected areas to laser light at a frequency below that of a UV spectrum.

15. A method of effecting coloration of a dental restoration to produce a desired color in selected areas of said dental restoration comprising the steps of:

(a) forming a mixture of powdered dental porcelain and a photonucleable silicate material;

(b) shaping said mixture into said dental restoration;

(c) heating said dental restoration to its fusing temperature and thereafter allowing said restoration to cool;

(d) exposing selected areas of said restoration to a first source of electromagnetic energy to establish color centers in said restoration;

(e) further exposing said selected areas to a second source of energy to cause color intensification of said color centers in said restoration to produce said desired color in said selected areas of said dental restoration; and (f) cooling said restoration after said desired color of said selected areas is produced to thus prevent further color intensification of said color centers in said dental restoration.

16. The method of claim 15 wherein said first source of energy comprises light in a specific frequency to establish said color centers.

17. The method of claim 16 wherein said second source of energy comprises heat.

18. The method of claim 16 wherein said second source of energy comprises light in a frequency different from said frequency of said first source.

*19. A method of effecting coloration of a dental restoration to produce a desired color in selected areas of said dental restoration comprising the steps of:*

*(a) forming a mixture of powdered dental porcelain and a photonucleable silicate material;*

*(b) shaping said mixture into a block and heating said block to its fusing temperature and thereafter allowing said block to cool;*

*(c) shaping said block into said dental restoration;*

*(d) exposing selected areas of said restoration to light of a specific wave length to establish color centers in said restoration;*

*(e) reheating said selected areas to a predetermined temperature sufficient to cause color intensification in said selected areas of said restoration and maintaining said predetermined temperature while said color intensifies and changes in said selected areas to produce said desired color in said selected areas; and*

*(f) cooling said restoration after said desired color of said selected areas is produced to thus prevent further color intensification of said color centers in said dental restoration.*

*20. A method of effecting coloration of a dental restoration to produce a desired color in selected areas of said dental restoration comprising the steps of:*

*(a) forming a mixture of powdered dental porcelain and a photonucleable silicate material;*

*(b) shaping said mixture into a block and heating said block to its fusing temperature and thereafter allowing said block to cool;*

*(c) shaping said block into said dental restoration;*

*(d) exposing selected areas of said restoration to a first source of electromagnetic energy to establish color centers in said restoration;*

*(e) further exposing said selected areas to a second source of energy to cause color intensification of said color centers in said restoration to produce said desired color in said selected areas of said dental restoration; and*

*(f) cooling said restoration after said desired color of said selected areas is produced to thus prevent further color intensification of said color centers in said dental restoration.*

* * * * *